US011850446B2

United States Patent
Shinton et al.

(10) Patent No.: US 11,850,446 B2
(45) Date of Patent: Dec. 26, 2023

(54) RADIOTHERAPY APPARATUS (71) Applicant: Elekta Limited, Crawley (GB)

(72) Inventors: Ian Shinton, Crawley (GB); Janusz Harasimowicz, Crawley (GB); George Chadwick, Crawley (GB); Paul Dixon, Crawley (GB)

(73) Assignee: ELEKTA LIMITED, Crawley (GB)

( * ) Notice: Subject to any disclaimer, the term of this patent is extended or adjusted under 35 U.S.C. 154(b) by 480 days.

(21) Appl. No.: 17/250,393

(22) PCT Filed: Jul. 15, 2019

(86) PCT No.: PCT/EP2019/069038
§ 371 (c)(1),
(2) Date: Jan. 15, 2021

(87) PCT Pub. No.: WO2020/016190
PCT Pub. Date: Jan. 23, 2020

(65) Prior Publication Data
US 2021/0290978 A1 Sep. 23, 2021

(30) Foreign Application Priority Data
Jul. 16, 2018 (GB) ...................................... 1811630

(51) Int. Cl.
A61N 5/10 (2006.01)
(52) U.S. Cl.
CPC ......... A61N 5/1049 (2013.01); A61N 5/1081 (2013.01); A61N 2005/1055 (2013.01); A61N 2005/1094 (2013.01)
(58) Field of Classification Search
CPC ...... A61N 5/1049; A61N 5/10; A61N 5/1081; A61N 2005/1094; A61N 2005/1055;
(Continued)

(56) References Cited

U.S. PATENT DOCUMENTS 6,975,895 B1 * 12/2005 Pelc ...................... H01J 35/153
600/411
10,561,377 B2 * 2/2020 Sossong ................. A61B 6/032
(Continued)

FOREIGN PATENT DOCUMENTS

CN 103800009 A 5/2014
CN 105073192 A 11/2015
(Continued)

OTHER PUBLICATIONS

"European Application Serial No. 1811630.1, Extended European Search Report dated Jan. 4, 2019", (dated Jan. 4, 2019), 4 pgs.
(Continued)

Primary Examiner — Irakli Kiknadze
(74) Attorney, Agent, or Firm — Schwegman Lundberg & Woessner, P.A.

(57) ABSTRACT

A radiotherapy apparatus adapted for use with a Magnetic Resonance Imaging (MRI) system, the radiotherapy apparatus comprising a linear accelerator, the linear accelerator including an electron source. In the linear accelerator electrons which are introduced by the source are accelerated to impact on a target and produce a beam of radiotherapeutic radiation. The linear accelerator has an accelerator waveguide within which the electrons are accelerated and an external waveguide enclosure; this enclosure extends substantially continuously over the accelerator waveguide. The waveguide enclosure is formed of a high magnetic permeability material and has a first aperture for the beam of radiotherapeutic radiation where the beam exits the waveguide enclosure and enters the MRI system and a second aperture for an RF guide for the introduction of electrons into the accelerator waveguide and for electrical lines for the particle source and coolant lines for the waveguide to pass through the enclosure and no other openings. The waveguide (Continued)

enclosure is preferably fabricated in a plurality of discrete parts.

16 Claims, 7 Drawing Sheets

(58) Field of Classification Search
CPC .. A61N 5/1042; A61N 5/1065; A61N 5/1067; A61N 2005/1088; A61N 5/1039; A61N 2005/1089; G12B 17/02; A61B 5/055; A61B 6/405; A61B 6/4064; G01R 33/421; G01R 33/28; G01R 33/42; G01R 33/4808; G01R 33/3806; G01R 33/34; G01R 33/385; G01R 33/4812; H05H 7/22; H05H 2277/11; Y02E 10/30; Y02E 10/38
USPC ...................................... 378/62–65
See application file for complete search history.

(56) References Cited

U.S. PATENT DOCUMENTS

| | | | | |
|---|---|---|---|---|
| 11,278,250 | B2* | 3/2022 | Wang | A61B 6/032 |
| 2011/0012593 | A1 | 1/2011 | Shvartsman et al. | |
| 2014/0266208 | A1 | 9/2014 | Dempsey et al. | |
| 2015/0146856 | A1* | 5/2015 | Beckman | A61N 5/1084 |
| | | | | 378/65 |
| 2017/0295638 | A1 | 10/2017 | Trail et al. | |

FOREIGN PATENT DOCUMENTS

| | | | |
|---|---|---|---|
| CN | 105664378 | A | 6/2016 |
| EP | 3307032 | A1 | 4/2018 |
| FR | 2246063 | A1 | 4/1975 |
| GB | 2551244 | A | 12/2017 |
| KR | 101378447 | B1 | 3/2014 |
| KR | 20150049316 | A | 5/2015 |
| KR | 20150049317 | A | 5/2015 |
| WO | WO-2005072825 | A1 | 8/2005 |
| WO | WO-2007045076 | A1 | 4/2007 |
| WO | WO-2011008969 | A1 | 1/2011 |

OTHER PUBLICATIONS

"International Application Serial No. PCT/EP2019/069038, International Search Report dated Oct. 15, 19", (dated Oct. 15, 2019), 4 pgs.
"International Application Serial No. PCT/EP2019/069038, Written Opinion dated Oct. 15, 2019", (dated Oct. 15, 2019), 4 pgs.
Whelan, Brendan, et al., "Passive magnetic shielding in MRI-Linac systems", Physics in Medicine & Biology 63.7, (2018), 31 pgs.
"Chinese Application No. 201980060505.8, First Office Action dated Dec. 9, 2022", (dated Dec. 9, 2022), 5 pgs.
"Chinese Application No. 201980060505.8, Search Report dated Dec. 5, 2022", (dated Dec. 5, 2022), 7 pgs.

* cited by examiner

*Fig 1*

Prior Art

RADIOTHERAPY APPARATUS

PRIORITY APPLICATIONS

This application is a U.S. National Stage Filing under 35 U.S.C. § 371 from International Application No. PCT/EP2019/069038, filed on Jul. 15, 2019, and published as WO2020/016190 on Jan. 23, 2020, which claims the benefit of priority to United Kingdom Application No. 1811630.1, filed on Jul. 16, 2018; the benefit of priority of each of which is hereby claimed herein, and which applications and publication are hereby incorporated herein by reference in their entirety.

FIELD OF THE INVENTION

The present invention relates to radiotherapy apparatus, particularly but not exclusively to Magnetic Resonance (MR) guided linear accelerator apparatus.

BACKGROUND ART

Radiotherapeutic apparatus is well-known, in which a source of radiation emits a beam of radiation that is directed toward a patient in order to destroy or otherwise harm cancerous cells within the patient. Many designs of radiotherapy apparatus employ a radiation source such as a linear accelerator (linac) for high-energy (MV) X-radiation, or an isotopic source such as Co-60 mounted on an elongate gantry arm that is rotatable around a patient support on which a patient can be placed for treatment. The source is rotatable so it can be rotated around the patient in order to irradiate the desired region from a number of different directions, thereby reducing the dose applied to healthy tissue outside the desired region. It is normal to collimate the beam so as to limit its spatial extent to a desired region within the patient (usually the tumour containing the cancerous cells or a sub-section of the tumour) and to avoid irradiating nearby healthy and/or sensitive tissue. An electronic portal imaging device (EPID) is often mounted to the gantry on the opposite side to the source so as to receive the beam once it has been attenuated by passage through the patient; this device produces an image which can be used for correctly aligning or calibrating the system, as well as for assessing the patient's location and the placement of the radiotherapeutic treatment.

There are many designs of radiotherapy apparatus, but an increasingly prevalent type utilises a rotatable radiation source such as a linear accelerator, mounted conventionally so as to be rotatable, in combination with a magnetic resonance imaging (MRI) system (the combination is known as a MRI/Linear Accelerator, "MR Linac", or MRL); incorporating a non-ionizing imaging technique such as MRI into radiotherapy allows real-time image guidance, and improves tumour targeting accuracy, enabling better avoidance of critical structures and reducing side effects. MRL systems allow tissue to be tracked online, and therapeutic radiation beams can be guided to their targets (which may be moving and deforming, such as when the patient breathes) with sub-millimetre precision during treatment. MRI scanners rely on the capacity of certain atomic nuclei to absorb and emit radio frequency energy when placed in an external magnetic field; in most MRI systems, the protons contained in water molecules in the human body are excited and create a signal which is processed to form an image of the materials of the body.

Figure 1:
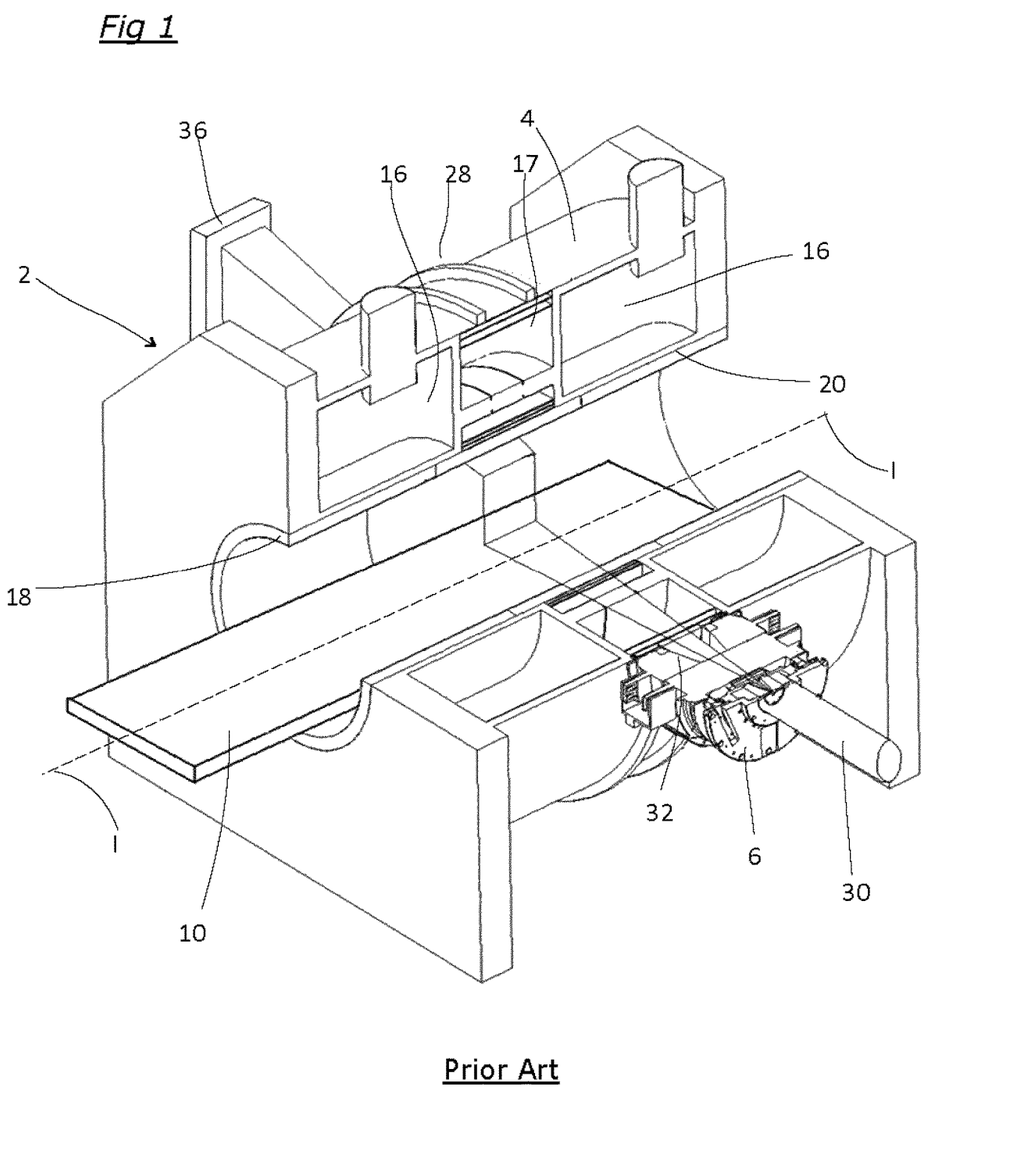
FIG. 1 is a schematic perspective view of a typical MRL system.

FIG. 1 shows a typical MRL system 2 comprising a linear accelerator radiotherapy apparatus 6 and a generally cylindrical magnetic resonance imaging (MRI) apparatus 4. The couch 10 is movable along a horizontal, translation axis (labelled "II"), such that a patient resting on the couch is moved into a cylindrical volume encircled by the rotatable radiotherapy apparatus and the MRI apparatus. The MRI apparatus 4 produces near real-time imaging of a patient positioned on the couch 10. The MRI apparatus includes a primary magnet 16 which acts to generate the so-called "primary" magnetic field for magnetic resonance imaging. That is, the magnetic field lines generated by operation of the magnet 16 run substantially parallel to the central translation axis II. The magnetic field produced by the magnet 16 is very powerful indeed—the strength of the field produced by a typical MRI magnet is in the order of 0.5 to 3.0 Tesla, or 5,000 to 30,000 Gauss (which compares to the Earth's magnetic field of about 0.5 Gauss). The primary magnet 16 consists of one or more coils with an axis that runs parallel to the translation axis II. The one or more coils may be a single coil or a plurality of coaxial coils of different diameter. In one arrangement (illustrated), the one or more coils in the primary magnet 16 are spaced such that a central window 17 of the magnet 16 is free of coils. In other arrangements, the coils in the magnet 16 may simply be thin enough that they are substantially transparent to radiation of the wavelength generated by the radiotherapy apparatus. The more sensitive parts of the system 2, such as the linear accelerator 6, are positioned in the region outside the magnet 16 where the magnetic field is weaker; however the field in this region is still considerable.

The MRI apparatus 4 further comprises two gradient coils 18, 20, which generate the so-called "gradient" magnetic field that is superposed on the primary magnetic field. These coils 18, 20 generate a gradient in the resultant magnetic field that allows spatial encoding of the protons so that their position can be determined, for example the gradient coils 18, 20 can be controlled such that the imaging data obtained has a particular orientation. The gradient coils 18, 20 are positioned around a common central axis II with the primary magnet 16, and are displaced from one another along that central axis. This displacement creates a gap, or window, between the two coils 18, 20. In an embodiment where the primary magnet 16 also comprises a central window between coils, the two windows are aligned with one another.

A radio frequency (RF) system (not shown) causes the protons to alter their alignment relative to the magnetic field. When the RF electromagnetic field is turned off the protons return to the original magnetization alignment. The RF system excites the protons (hydrogen atoms) in the patient's body at an appropriate resonance frequency (for hydrogen in a 1.5 Tesla field the resonant frequency is approximately 64 MHz) to produce alternating alignment changes and create a small MR signal which can be detected by scanning. The RF system may include a single coil that both transmits the radio signals and receives the reflected signals, dedicated transmitting and receiving coils, or multi-element phased array coils, for example. Control circuitry controls the operation of the various coils 16, 18, 20 and the RF system, and signal-processing circuitry receives the output of the RF system, generating therefrom images of the patient supported on the couch 10. For accurate imaging, the reception side of the RF system must be sensitive and have the best possible signal to noise ratio. Accordingly the MR system is usually shielded from external fields so as to preserve and enhance imaging accuracy.

The MRL system 2 further comprises a radiotherapy apparatus 6 which delivers doses of radiation to a patient supported by the couch 10. The majority of the radiotherapy apparatus 6, including at least a source of radiation 30 (e.g. a linear accelerator and an x-ray target) and a multi-leaf collimator (MLC) 32, is mounted on a gantry or chassis 28. The gantry 28 is continuously rotatable around the couch 10 when it is inserted into the treatment area, powered by one or more motors (not shown). In the illustrated embodiment, a radiation detector 36 is also mounted on the gantry 28 opposite the radiation source 30 and arranged to rotate at the same time as the radiotherapy apparatus so as to keep the rotational axis of the gantry positioned between them. The radiotherapy apparatus 6 further comprises control circuitry, which may be integrated within the system 2 shown in FIG. 1 or remote from it, and controls the movements and operation of the radiation source 30, the MLC 32 and the chassis motor.

Linear accelerators include a source of subatomic particles (usually electrons) and a means to initiate their movement along a linear axis. High voltage electrodes are aligned along the axis of an accelerator waveguide and these electrodes are energised at radio frequencies to increase the kinetic energy of the particles moving along the accelerator axis; the particles are subjected to a series of oscillating electric potentials along the linear axis, so accelerating the particles to near-relativistic velocities. In radiotherapy apparatus the accelerated particles impact on a target of high density material, such as tungsten, to produce X-rays which can be collimated into a beam and this beam directed for therapy. Many linear accelerators used in radiotherapy have tuned-cavity waveguides comprising a series of accelerating cavities arranged linearly along the particle beam axis; a series of electrically isolated electrodes accelerate the particles along the axis, and the electrodes are energised by radio frequency (RF) energy energises. The RF energy is conducted from an RF source and introduced into the waveguide by an RF waveguide, and concentrated within the accelerator waveguide as either a standing wave or a travelling wave (based on the particular RF design). Because of the very high energy levels employed in this process, significant heat is generated within the accelerator waveguide and this heat needs to be removed by a suitable cooling system, usually a liquid cooling system. The waveguide is also used to contain and accurately direct the beam of particles; this is important, because if the particle beam is not accurately directed its impact on the target may not be within design parameters, defocusing the beam or changing its position such that the linear accelerator does not operate properly and the resulting radiation is out of specification. In extreme cases of beam deviation, when beam power exceeds several kilowatts (continuous wave power), the accelerator can be damaged. Electrons are very sensitive to low frequency magnetic fields, so are easily affected by the typically strong magnetic field immediately outside the MR system in a MRL. Whilst linear accelerators are normally contained within a steel pressure vessel, which provides a certain amount of magnetic shielding, preventing the moving electrons from being deflected whilst moving through the waveguide is a significant problem.

In addition, the sensitivity of the MR imaging process can be adversely affected by the presence in a MRL of a linear accelerator. The high voltages used in the linear accelerator waveguide can introduce signal noise into the MR RF sensing system and affect the small MR signals sensed by the RF system receiver, thus reducing the MR imaging quality.

SUMMARY OF THE INVENTION

The present invention is founded on a realisation that a suitable magnetic shield in a MRL can simultaneously address the problems of preventing linear accelerator beam deflection caused by the high static magnetic field of the MR system and of the high voltages used in linear accelerators adversely affecting MR image quality, Accordingly, the present invention provides a radiotherapy apparatus adapted for use with a Magnetic Resonance Imaging (MRI) system, the apparatus comprising a linear accelerator adapted to be mounted to an exterior surface of the MRI system and having an accelerator waveguide within which electrons/particles from a source of electrons (or other particles) are accelerated to impact on a target and produce a beam of radiotherapeutic radiation, the apparatus having an external waveguide enclosure which extends substantially continuously around the exterior of the accelerator waveguide, the waveguide enclosure being formed of high magnetic permeability material, and having a first aperture for the beam of radiotherapeutic radiation where the beam exits the waveguide enclosure and enters the MRI system and a second aperture for an RF guide for the introduction of electrons into the accelerator waveguide and for electrical cabling and coolant lines for the waveguide accelerator to pass through the enclosure, wherein an interface flange is provided for mounting between on the one side the accelerator waveguide and the waveguide enclosure and on the other side the exterior of the MRI system, the flange including a waveguide enclosure end cap formed of high magnetic permeability material in which the first aperture is located, there being essentially no further apertures or breaks in the waveguide enclosure.

Such an enclosure, or can, of high magnetic permeability material provides a continuous low reluctance path for magnetic flux around substantially the entire periphery of the linear accelerator (the only breaks in the continuous high magnetic permeability material being the two apertures) and so provides an effective magnetic shield around the linear accelerator against static or slowly varying magnetic fields such as those typically present outside but close to a MRL. The high permeability material, provides a path for the magnetic, field lines outside and adjacent to the MRI system around the volume surrounded by the enclosure, in effect conducting the magnetic field around the waveguide enclosure and preventing it from penetrating inside the enclosure, thus shielding the waveguide within and the accelerating electrons/particles from the effects of the MRI system magnetic field, and this shielding effect is greater due to the continuous nature of the enclosure. The waveguide enclosure is also effective to reduce the effects of the varying magnetic field created by the system accelerating the electrons/particles on the MR. RF sensing system and so help prevent degradation of the MR imaging quality.

The optimal shape of waveguide enclosure to maximise conduction of magnetic field and so give maximum shielding would be a sphere; this is because the magnetic field flows through the high permeability material in a manner similar to a liquid flow, and discontinuities in the flow path lead to leakage, reducing shielding efficiency. A spherical waveguide enclosure would not be space-efficient, but the major dimension of a linear accelerator is along its linear axis, and we have found that a suitable compromise between the elimination of discontinuities in the shape of the wave guide enclosure which is still effective in preventing flux leakage and is reasonably straightforward to manufacture is for the cross-section of the enclosure transverse to the linear axis to be continuously curved, with substantially no discontinuities in shape. Thus the waveguide enclosure could be cylindrical, and not necessarily circular in cross-section (it could be oval or even pear-shaped in cross-section). The "cylindrical" enclosure could be closed at either end by planar, stepped or curved end caps of high magnetic permeability material (the end cap adjacent the MRI system is the interface flange), which are easy to manufacture and to fix to the enclosure—such an arrangement would produce a discontinuity where the end caps meet around the end circumference of the enclosure, but we have found that in practice the flux leakage such a discontinuity allows is small, and can be predicted and compensated for by other design features—the cylindrical parts and the end caps are manufactured with precise dimensions so that where they meet they are in substantially continuous contact around the entire circumference of the cylindrical parts.

The enclosure may be fabricated in a plurality of separate or discrete parts, provided that it extends over substantially all of the accelerator waveguide so as to provide maximum shielding of the linear accelerator. The non-unitary (i.e. formed of several separate parts joined together to form a substantially continuous shield) nature of the waveguide enclosure is deliberate, as this facilitates manufacture and installation of the enclosure, and installation, maintenance and replacement of the linear accelerator it shields; however, such an arrangement can also adversely affect the magnetic flux path through the enclosure and its ability to shield the linear accelerator it encases. It is therefore important that the separate parts of the waveguide enclosure are solidly but releasably connected together, in such a way that there are no gaps through which magnetic field lines could penetrate or from which magnetic flux could leak. The separate parts are preferably formed with overlapping joints, and abutting surfaces are preferably complementarily shaped and/or of complex, labyrinthine shape (so that the path from the interior to the exterior of the waveguide is labyrinthine, so that the path curves back on itself, for example) so as to minimise magnetic flux leakage. Such leakage may be further limited by ensuring that overlapping joints are fillet welded together, and/or joined by extensive arrays of mechanical fasteners (also preferably of high permeability material).

The enclosure may have an outwardly-extending collar portion, and this is preferably sized and configured to surround the RF guide, the piping and the cabling over at least a part of their length extending away from the enclosure. This collar helps prevent electromagnetic field leakage into or out of the waveguide enclosure, and the more tightly the collar wraps around the RF guide, the piping and the cabling the more effective the reduction in leakage. It may be suitable for the collar portion to have in cross-section a portion surrounding the RF guide (which is usually square or rectangular) and an adjacent (preferably contiguous) protrusion which surrounds the piping and cabling. This enables the cross-sectional area of the collar to be minimised and thus minimises leakage. The protrusion can be sized and configured to allow the piping and cabling to, run largely parallel within the collar portion, which means that any electromagnetic leakage must travel along the collar and, as this can be oriented so as to point away from the waveguide accelerator and the MRI system, this reduces the effects of any leakage between these elements. As with the main part of the waveguide enclosure surrounding the linear accelerator, the design of this collar should minimise discontinuities in shape, accordingly the collar is curved gently—i.e. it has, in cross-section, rounded corners.

BRIEF DESCRIPTION OF THE DRAWINGS

The invention will now be described by way of example and with reference to the accompanying figures, in which.

DETAILED DESCRIPTION OF THE EMBODIMENTS

Figure 2:
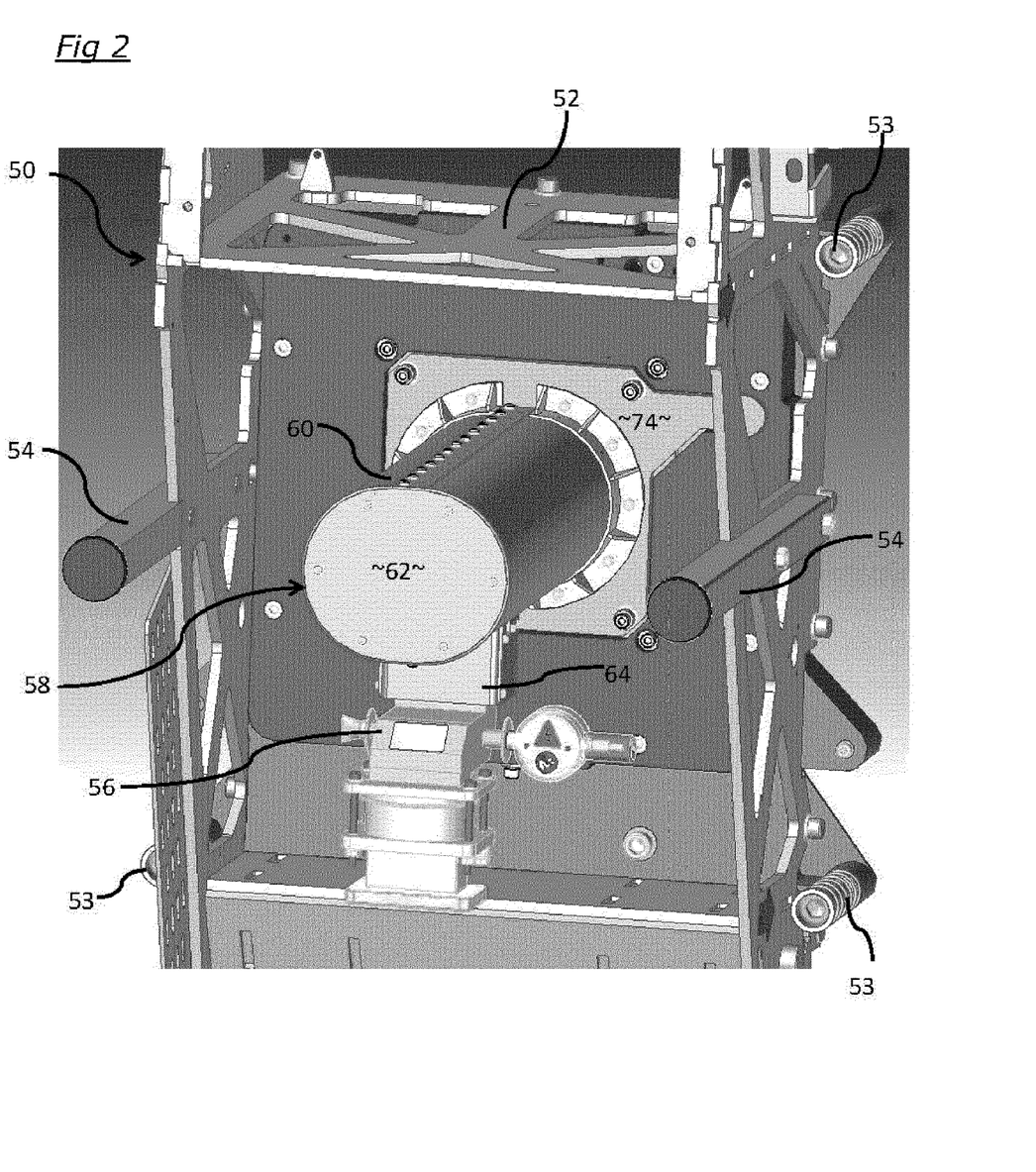
FIG. 2 is a schematic perspective view of a linear accelerator assembly for use with an MRL system such as that of FIG. 1 and incorporating a waveguide enclosure in accordance with the present invention.
Figure 3A:
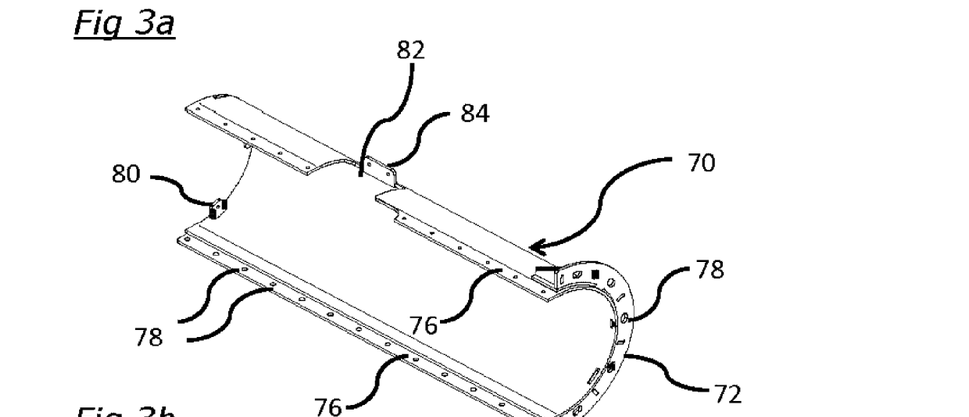
FIGS. 3*a*, 3*b* and 3*c* are perspective views of parts of the waveguide enclosure shown in FIG. 2.
Figures 3B, 3C:
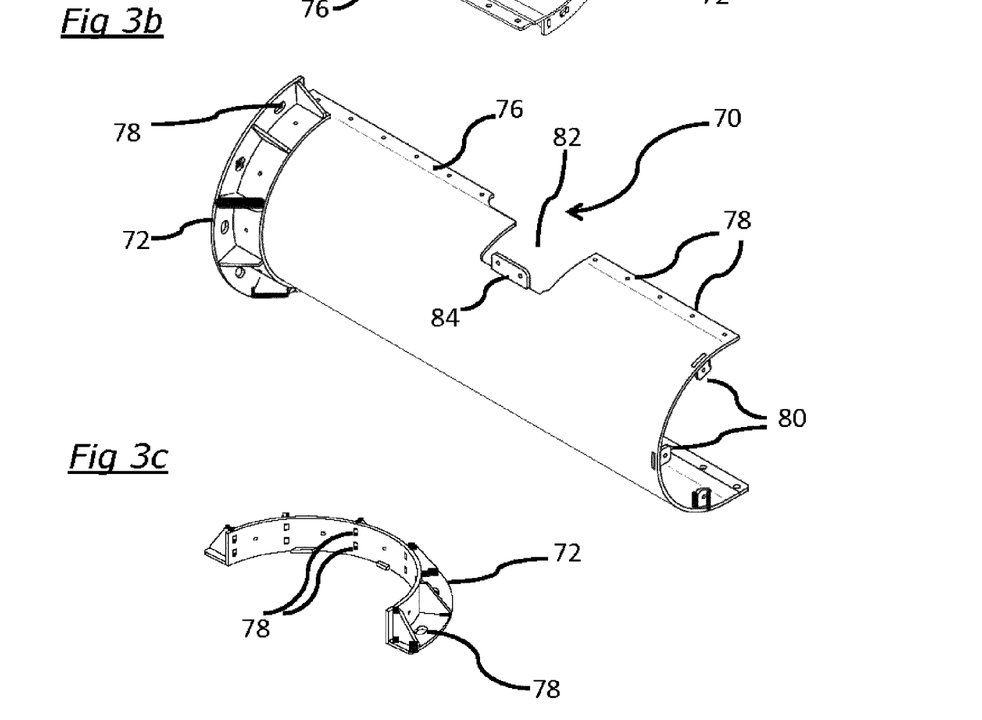
Figure 6:
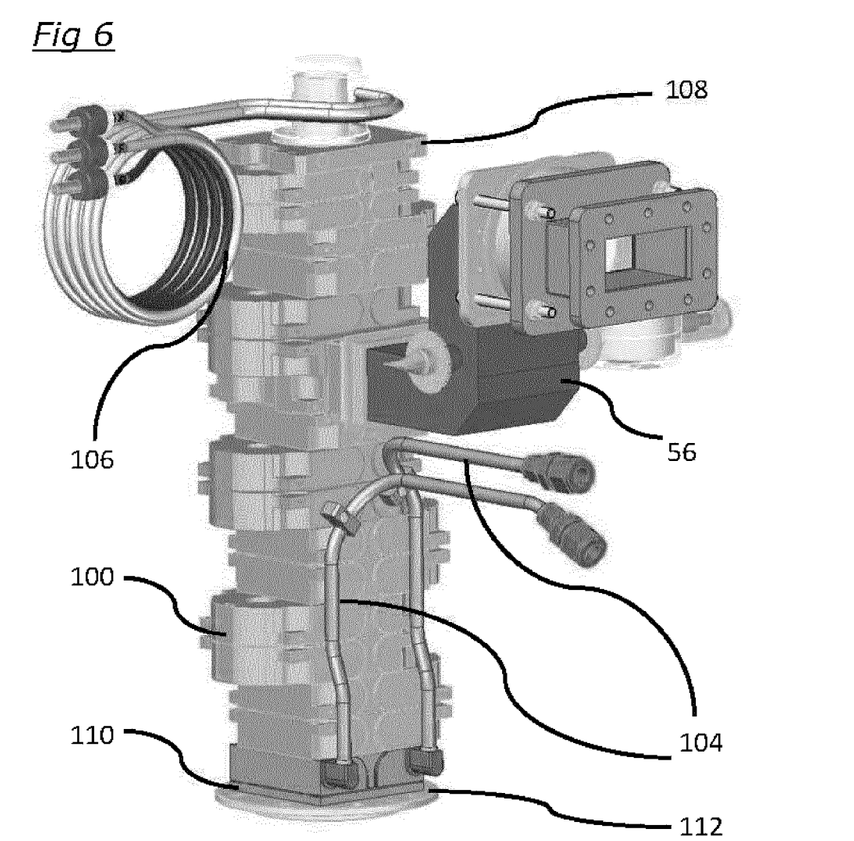
FIG. 6 is a schematic perspective view of the accelerator waveguide and RF guide of FIG. 1 without their surrounding waveguide enclosure.
Figure 8A:
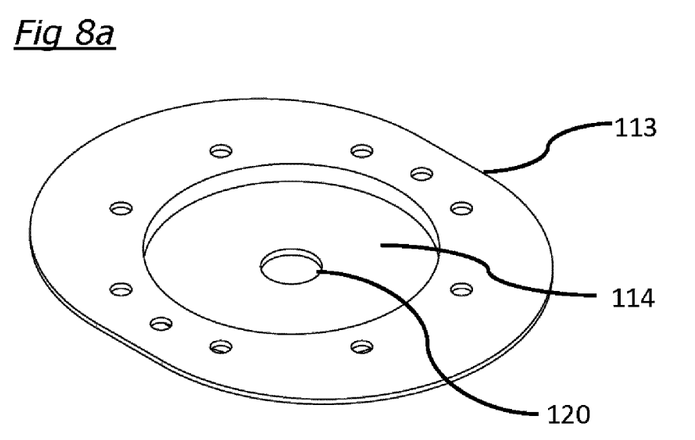
FIG. 8*a* is a schematic perspective view of the waveguide enclosure end cap.

The conventional MRL system shown in FIG. 1 is described above. FIG. 2 shows a linear accelerator assembly 50 which is enclosed in an open framework or cradle 52 for mounting to the rotatable gantry 28 of the MRL by way of attachments 53; although not shown in FIG. 2, the gantry would be behind the assembly 50 shown in FIG. 2, with the legs 54 extending generally radially outwardly from the axis II of the MRI apparatus (as shown in FIG. 1). The linear accelerator comprises an RF guide 56 for electrons emitted by an electron source (not shown) which causes electrons to be injected upwardly in the drawing to a linear accelerator waveguide 100 (which is not visible in FIG. 1 because it is hidden within the waveguide enclosure 58, but is shown in FIG. 6) but the waveguide turns the electrons so that they move in a different direction, and accelerates the electrons radially inwardly with respect to the MRI system, into the plane of the drawing, roughly parallel with the legs 54. The enclosure 58 has a generally cylindrical portion 60, which has an end cap 62 at the end of the cylinder distant from the MRI system and a second end cap 113 (described further below with reference to FIGS. 8*a* and 8*b*) at the end closest to the MRI system, and a mostly rectangular-section collar portion 64 which extends upwardly from the RF guide 56 and is secured to the cylindrical portion 60 so as to provide a continuous magnetic shield to encase the waveguide with no gaps for magnetic field leakage to take place. For ease of installation, the enclosure is fabricated as shown in FIG. 3: FIGS. 3*a* and 3*b* show one part 70 of the cylindrical portion 60 of the enclosure 58, and FIG. 3*c* shows an end flange 72 which is used to secure the enclosure 58 to a plate 74 which extends to cover the central window 17 of the MRL. Each cylindrical part 70 has edge flanges 76 which are configured so as to overlap and fit smoothly against complementarily-shaped edge flanges provided on another part of the enclosure 58 to provide a magnetically sealed whole. The cylindrical parts 70 of the enclosure are releasably fixed together by mechanical fixings (not shown), such as nuts and bolts which are disposed along the overlapping edge flanges 76 in a linear array (as shown by the holes 78 in FIG. 3), and there are generally more provided than is required to provide a purely mechanical joint, but enough so as to ensure sufficient contact between the parts to ensure that there is a continuous low reluctance flux path with no gaps for flux leakage. Lugs 80 are provided for fixing the end cap 62 to the cylindrical portion 60. The semi-circular end flange 72 is similarly fixed to one end of the cylindrical portion 60, and/or it may be fillet welded thereto (and the end flange may be fabricated using similar fillet welds). An opening 82 is formed along the longitudinal edge of the cylindrical parts 70 for attaching the collar portion 64 of the waveguide enclosure 58 to the cylindrical portion 60, via lugs 84 and mechanical fixings (not shown), and for the passage of coolant pipes and electrical cabling, as will be described below. As shown in FIG. 3 the overlapping edge flanges 76 are flat, however their resistance to flux leakage can be increased if, when joined, they form a complementary convoluted (i.e. non-flat) shape, so that for flux to leak between the joined flanges it would have to follow a labyrinthine path.

The waveguide enclosure 58 and the collar 64, and preferably also the mechanical fixings, are formed of a suitable high magnetic permeability material. There are many compositions for such materials, but we have found that suitable compositions are made of approximately 77% nickel, 4.8% copper, 14.9% iron and 1.5% chrome, or approximately 77% nickel, 16% iron, 5% copper and 2% chromium or molybdenum, or approximately 80% nickel, 5% molybdenum, small amounts of various other elements such as silicon, and the remaining 12 to 15% iron. The waveguide enclosure 58 is fabricated so as to be relatively straightforward to assemble around the waveguide and for removal/exchange/maintenance of the accelerator waveguide and other elements within the enclosure; the permeability of the material is easily degraded by fairly slight mechanical impacts, and to restore it to its design permeability requires quite specific heat treatment (usually at a high temperature in a dry, inert or hydrogen atmosphere for a reasonable time, followed by a specific cooling rate back to ambient temperature), so it is important that the enclosure is designed so that it can be put together and disassembled easily and without being subjected to accidental mechanical impacts to allow the waveguide to be accessed easily for maintenance, etc.

Returning to FIG. 2, it will be seen that the open framework 52 surrounds the waveguide enclosure 58; this provides a measure of protection for the enclosure against accidental blows or impacts which might impair its magnetic permeability. We have found that a desirable arrangement is one in which, when the attachment fixings 53 are released, the cradle 52 pivots about a hinge (not shown) having an axis parallel to a line between the two lowermost fixings 53. This allows the linear accelerator assembly 50 to be swung away from the MRI system to allow access to the target end of the linear accelerator. In order to protect the waveguide enclosure 58 from damage in this state, the legs 54 extend for a distance longer than the length of the cylindrical portion 60, so that when the assembly 50 is swung open, the legs 54 can be allowed to rest on the floor whilst holding the end plate 62 above the floor, the weight of the assembly 50 being held by the hinge and the legs 54.

Figure 4:
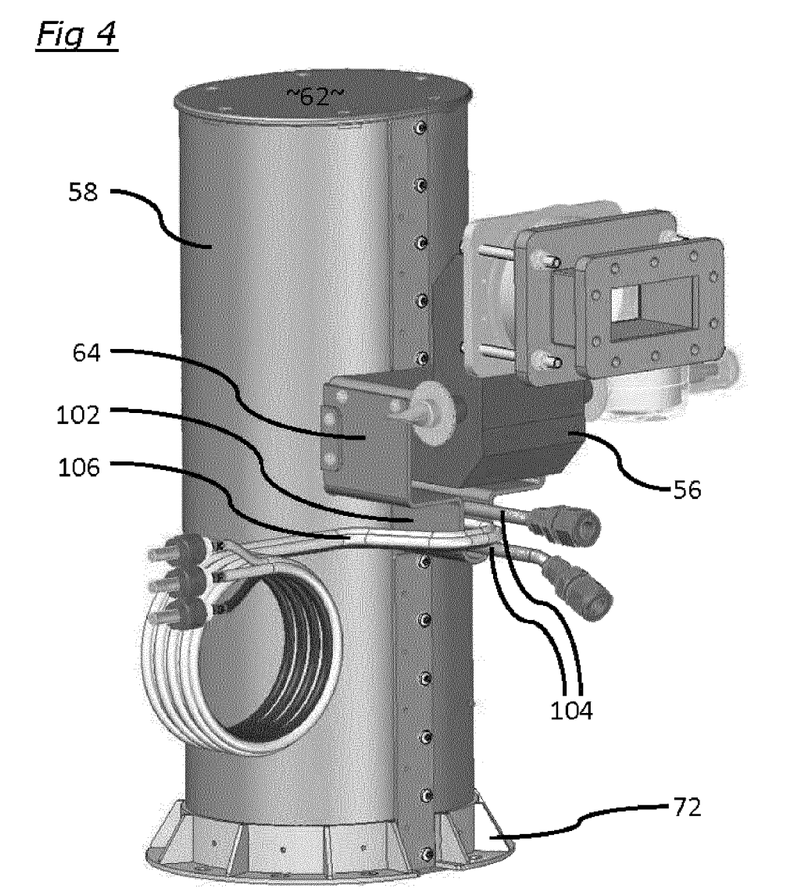
FIG. 4 is a schematic perspective view of the waveguide enclosure and RF guide of FIG. 2.
Figure 5:
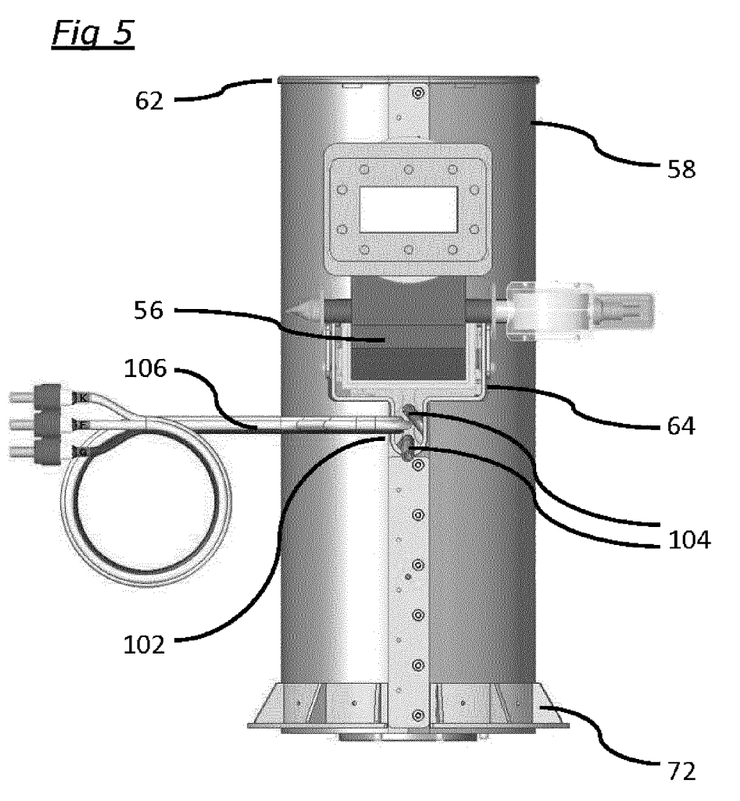
FIG. 5 is another schematic view of the waveguide enclosure and RF guide of FIG. 4.

Referring now to FIGS. 4 and 5, it can be seen that in cross-section the collar portion 64 is mostly rectangular, but that it has a protrusion 102; the rectangular part of the collar portion 64 is sized and, configured as shown in FIG. 5 so as to closely surround the RF guide 56 (which, as is usual, is rectangular in cross-section); the corners of the rectangular part are curved. The protrusion 102 surrounds the coolant piping 104 and the electrical cabling 106 which are necessary for the operation of the waveguide inside the enclosure 58. The protrusion 102 is sized and configured so as to form a kind of trunking, which allows the piping 104 and cabling 106 to run largely parallel out of the enclosure and away from the waveguide closely adjacent to the RF guide 56, with the protrusion 102 having a cross-section which is curved and as small as possible and at the same time minimising the area of the opening 82 (see FIGS. 3a and 3b) in the enclosure 56. Making the opening 82 and the cross-sectional area of the protrusion 102 as small as possible minimises magnetic field leakage out of/into the enclosure whilst still enabling the accelerator waveguide to be removed/replaced without having to disassemble the entire enclosure 58 (instead only the end cap 62 could be removed so that the accelerator waveguide 100 can be withdrawn and the piping 104 and cabling 106 manoeuvred through the protrusion 102 and into/out of the hole 82. Further, as the coolant pipes 104 have a cool inlet side and a hot outlet side, placing the cabling 106 between these helps prevent undesirable heat transfer between the pipe runs, and the piping 104 simultaneously provides a small amount of shielding in addition to the material of the protrusion 102 guarding against electromagnetic field leakage from the cabling 106.

FIG. 6 shows the accelerator waveguide 100, details of the construction and design of which have no direct relation to the present invention. The linear accelerator waveguide 100 has one end 108 to which the electrical cabling 106 supplies electrical power and control signals and a second end 110 adapted to be mounted against the exterior of an MRI system. The RF guide 56 introduces particles to be accelerated at a point along the linear axis of the accelerator waveguide between the ends 108, 110, and coolant pipes 104 are mounted to the accelerator waveguide to allow a flow of a fluid for cooling purposes.

Figure 7:
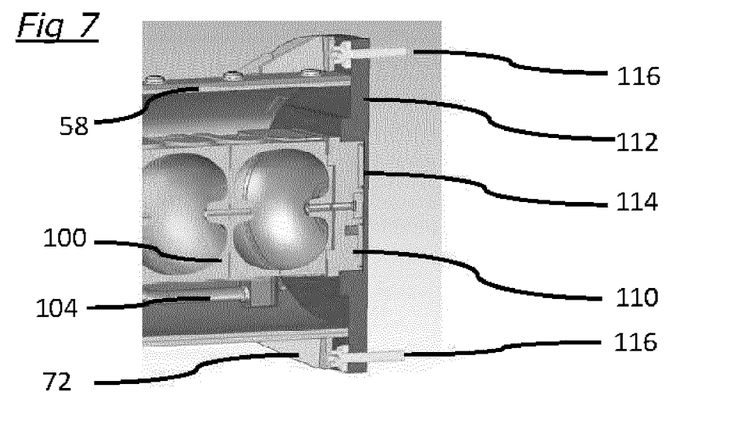
FIG. 7 is a schematic cross-sectional view illustrating how the accelerator waveguide and waveguide enclosure of FIGS. 4 to 6 may be mounted to an MRI system.
Figure 8B:
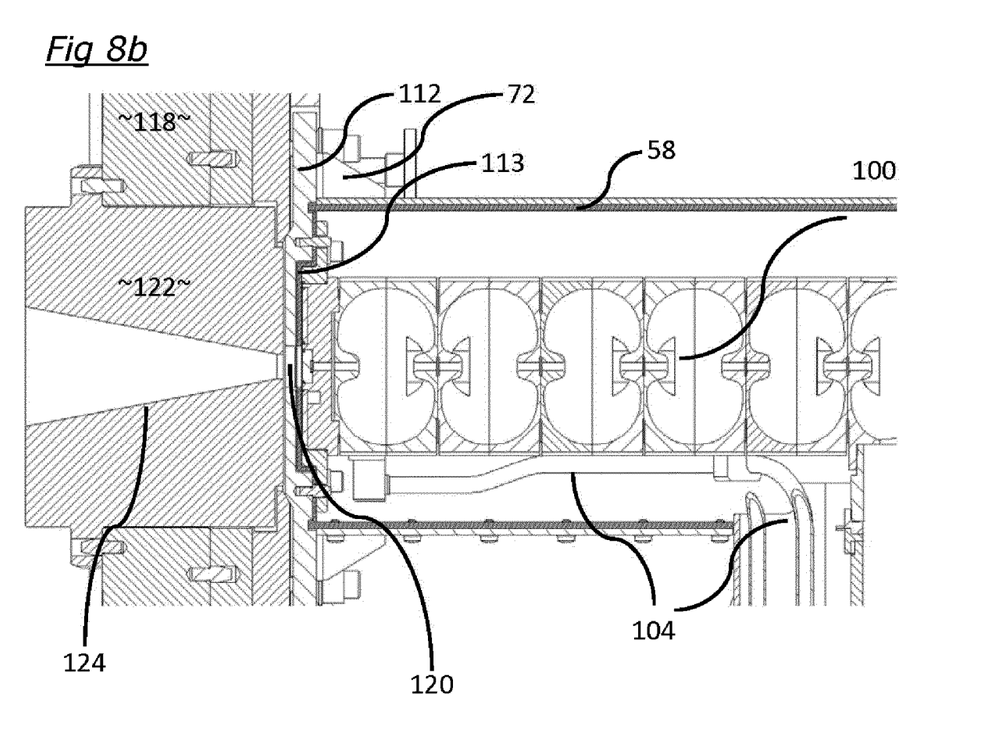
FIG. 8*b* is a schematic cross-sectional view illustrating the end cap in position.

FIG. 7 shows how the accelerator waveguide and waveguide enclosure may be mounted to an MRI system; the end flanges 72 of the enclosure 58 are mounted to an interface flange 112, which includes an end cap 113 (not shown in FIG. 7, see FIGS. 8a and 8b) made of high magnetic permeability material, and which is adapted so as to mount directly to the exterior surface of the MRI system. End cap 113 completes the electromagnetic shielding provided by the enclosure 58 and it is manufactured with dimensional precision so as to be substantially continuously contiguous with the cylindrical parts 70 of the enclosure 58; the flange 112 is adapted to align the linear accelerator with the MRI system (a part of the outer wall 118 of the MRI is shown in FIG. 8b), and is sized so as to distance the fixings 116 for mounting the flange to the MRI system from the shielded volume provided by the enclosure 58 and end cap 113. The central portion 114 of end cap 113, has a central aperture 120 to allow the beam of radiation produced by the linac to enter the MRI system (part of the outer wall of which is shown at 118). A block of shielding material 122 with a conical hole 124 is provided for the beam to enter the MRI system and to prevent field leakage into the waveguide enclosure 58. The provision of hole 120 prevents beam hardening effects and scatter which would be caused were the material of the end cap 113 to be in the beam path; the beam aperture 120 is designed to be sufficiently small so as to ensure that there is no appreciable field leakage into the waveguide enclosure (noting also that the particles in the beam as they enter aperture 120 are moving at close to relativistic speeds and are thus far less affected by the magnetic field of the MRI system than they would be at lower speeds—at the injector section end of the accelerator waveguide 100, to the right of FIG. 8b for example). The aperture should be no larger than the diameter of the beam in ambient magnetic field (i.e. about 0.5 Gauss), in practice we have found that a diameter of about 20 mm is suitable for aperture 120, but it could be smaller (10 mm or 15 mm, for example) or larger (25 mm or 30 mm, for example).

It will of course be understood that many variations may be made to the above-described embodiment without departing from the scope of the present invention. For example, the waveguide enclosure is illustrated as having two generally semi-circular cylindrical portions and a rectangular portion, but it will be understood that there could be a greater number of parts, of different shapes, provided that they are relatively easy to manufacture and assemble, and can provide a suitably good seal to prevent magnetic flux leakage. We have described how the entire waveguide assembly is formed of a high magnetic permeability material, and given an example in which the material is the same for all parts of the enclosure, including the fittings. It will be understood that constituent parts of the enclosure could be formed of different high permeability materials, tailored according to the prevailing magnetic flux at different positions relative to the MRI system. In addition, different parts of the enclosure could be of different thicknesses, so as to provide preferential flux paths. The provision of only a single hole or break in the waveguide enclosure in addition to the beam aperture is desirable because as well as minimising flux leakage it facilitates manufacture and assembly; however, the skilled person would understand that the provision of separate, smaller holes for each of the RF guide, electrical cabling and coolant lines would further reduce the possibility of electromagnetic field leakage (albeit at the cost of increased manufacturing/assembly complexity) and therefore such individual holes, provided that they are closely adjacent, should be regarded as within the scope of this invention. For ease of assembly, the path for the piping and cabling within the protrusion part of the collar is preferably straight and directed away from the accelerator waveguide; this path could instead be curved or labyrinthine, and/or directed at any angle away from the waveguide, which would further restrict electromagnetic field leakage even if this were at the cost of reduced ease of manufacture/assembly. There could be a thin layer of high magnetic permeability material extending across the first aperture, which would further reduce magnetic field leakage, but this would attenuate the beam and cause a certain amount of beam scatter. The beam aperture is circular and the hole conical, however other beam cross-sections and complementary hole shapes are possible.

Where different variations or alternative arrangements are described above, it should be understood that embodiments of the invention may incorporate such variations and/or alternatives in any suitable combination.

The invention claimed is:

1. A radiotherapy apparatus adapted for use with a Magnetic Resonance Imaging (MRI) system, the apparatus comprising:
   a linear accelerator adapted to be mounted to an exterior surface of the MRI system and having an accelerator waveguide within which electrons from a source are accelerated to impact on a target and produce a beam of radiotherapeutic radiation; and
   an external waveguide enclosure which extends substantially continuously around the accelerator waveguide, the waveguide enclosure being formed of high magnetic permeability material, the waveguide enclosure including:
   a first aperture for the beam of radiotherapeutic radiation where the beam exits the waveguide enclosure and enters the MRI system;
   a second aperture for an RF guide configured for introduction of the electrons into the accelerator waveguide, for an electrical line from the source and a coolant line for the waveguide to pass through the waveguide enclosure; and
   an interface flange for mounting is located between, on one side of the flange, the accelerator waveguide and the waveguide enclosure and on the other side of the flange the exterior of the MRI system, wherein the flange includes a waveguide enclosure end cap formed of high magnetic permeability material in which the first aperture is located.

2. The radiotherapy apparatus according to claim 1, wherein the waveguide enclosure has a longitudinal axis which, when the apparatus is in use, is substantially parallel to the linear accelerator, and wherein a cross-section of the waveguide enclosure in a plane transverse to the axis is continuously curved.

3. The radiotherapy apparatus according to claim 1, wherein the waveguide enclosure has an outwardly-extending collar portion which is sized and configured to surround the RF guide, and at least a portion of the electrical line and the coolant line extending away from the enclosure.

4. The radiotherapy apparatus according to claim 3, wherein the collar portion has in cross-section a portion surrounding the RF guide and an adjacent protrusion which surrounds at least a portion of the electrical line and the coolant line.

5. The radiotherapy apparatus according to claim 4, wherein the protrusion is sized and configured to allow the electrical line and the coolant line to run substantially parallel within the collar portion.

6. The radiotherapy apparatus according to any claim 1, wherein the waveguide enclosure is fabricated in at least two of separate parts.

7. The radiotherapy apparatus according to claim 6, wherein the separate parts are joined together with at least two overlapping joints.

8. The radiotherapy apparatus according to claim 7, wherein a first surface and a second surface of the at least two overlapping joints are complementarily shaped where the first surface and the second surface overlap.

9. The radiotherapy apparatus according to claim 7, wherein the overlapping joints are joined by fillet welds.

10. The radiotherapy apparatus according to claim 7, wherein the overlapping joints are joined by mechanical fixings.

11. The radiotherapy apparatus according to claim 1, wherein the apparatus is mounted to a gantry located so as to rotate around a central axis of the MRI system.

12. The radiotherapy apparatus according to claim 1, wherein the beam of radiotherapeutic radiation is directed towards a central axis of the MRI system.

13. The radiotherapy apparatus according to claim 11 or 12, wherein the linear accelerator is releasably fixed to the gantry by a mounting which selectably permits the linear accelerator to rotate about an axis substantially parallel to the central axis of the MRI system.

14. The radiotherapy apparatus according to claim 13, wherein the mounting comprises one or more longitudinal guard members which are longer than the waveguide enclosure.

15. A radiotherapy apparatus with a linear accelerator mounted to an exterior surface of a Magnetic Resonance Imaging (MRI) system, the apparatus comprising:
- an accelerator waveguide within which electrons from a source are accelerated to impact on a target and produce a beam of radiotherapeutic radiation; and
- an external waveguide enclosure which extends substantially continuously around the accelerator waveguide, the waveguide enclosure being formed of high magnetic permeability material, the waveguide enclosure including:
  - a first aperture for the beam of radiotherapeutic radiation where the beam exits the waveguide enclosure and enters the MRI system;
  - a second aperture for an RF guide configured for introduction of the electrons into the accelerator waveguide, for an electrical line from the source and a coolant line for the waveguide to pass through the waveguide enclosure; and
  - an interface flange for mounting is located between, on one side of the flange, the accelerator waveguide and the waveguide enclosure and on the other side of the flange, the exterior of the MRI system, wherein the flange includes a waveguide enclosure end cap formed of high magnetic permeability material in which the first aperture is located.

16. A radiotherapy apparatus adapted for use with a Magnetic Resonance Imaging (MRI) system, the apparatus comprising:
- a linear accelerator adapted to be mounted to an exterior surface of the MRI system and having an accelerator waveguide within which electrons from a source are accelerated to impact on a target and produce a beam of radiotherapeutic radiation; and
- an external waveguide enclosure which extends substantially continuously around the accelerator waveguide, the waveguide enclosure being formed of high magnetic permeability material, the waveguide enclosure including:
  - a first aperture for the beam of radiotherapeutic radiation where the beam exits the waveguide enclosure and enters the MRI system;
  - a second aperture for an RF guide configured for introduction of the electrons into the accelerator waveguide, for an electrical line from the source and a coolant line for the waveguide to pass through the waveguide enclosure; and
  - an interface flange for mounting is located between, on one side of the flange, the accelerator waveguide and the waveguide enclosure and on the other side of the flange the exterior of the MRI system, wherein the flange includes a waveguide enclosure end cap formed of high magnetic permeability material in which the first aperture is located;

wherein the waveguide enclosure has a longitudinal axis which, when the apparatus is in use, is substantially parallel to the linear accelerator, and wherein a cross-section of the waveguide enclosure in a plane transverse to the axis is continuously curved, wherein the waveguide enclosure has an outwardly-extending collar portion which is sized and configured to surround the RF guide, and at least a portion of the electrical line and the coolant line extending away from the enclosure, wherein the collar portion has in cross-section a portion surrounding the RF guide and an adjacent protrusion which surrounds at least a portion of the electrical line and the coolant line, wherein the protrusion is sized and configured to allow the electrical line and the coolant line to run substantially parallel within the collar portion, wherein the waveguide enclosure is fabricated in at least two separate parts, wherein the separate parts are joined together with at least two overlapping joints, wherein a first surface and a second surface of the at least two overlapping joints are complementarily shaped where the first surface and the second surface overlap, wherein the apparatus is mounted to a gantry located so as to rotate around a central axis of the MRI system, wherein the beam of radiotherapeutic radiation is directed towards a central axis of the MRI system, wherein the linear accelerator is releasably fixed to the gantry by a mounting which selectably permits the linear accelerator to rotate about an axis substantially parallel to the central axis of the MRI system, and wherein the mounting comprises one or more longitudinal guard members which are longer than the waveguide enclosure.

* * * * *

UNITED STATES PATENT AND TRADEMARK OFFICE
CERTIFICATE OF CORRECTION

PATENT NO. : 11,850,446 B2
APPLICATION NO. : 17/250393
DATED : December 26, 2023
INVENTOR(S) : Shinton et al.

Page 1 of 1

It is certified that error appears in the above-identified patent and that said Letters Patent is hereby corrected as shown below:

In the Claims

In Column 10, Line 38, in Claim 6, after "to", delete "any"

In Column 10, Line 40, in Claim 6, before "separate", delete "of"

Signed and Sealed this
Eleventh Day of February, 2025

Coke Morgan Stewart
*Acting Director of the United States Patent and Trademark Office*